(12) United States Patent
Wang et al.

(10) Patent No.: US 10,520,387 B2
(45) Date of Patent: Dec. 31, 2019

(54) GAS LEAKAGE TREATMENT METHOD AND AERIAL VEHICLE

(71) Applicant: SZ DJI TECHNOLOGY CO., LTD., Shenzhen (CN)

(72) Inventors: Qiguang Wang, Shenzhen (CN); Yao Li, Shenzhen (CN); Yongjian Zhao, Shenzhen (CN); Hui Sun, Shenzhen (CN); Yuanzhen Guo, Shenzhen (CN)

(73) Assignee: SZ DJI TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/582,025

(22) Filed: Apr. 28, 2017

(65) Prior Publication Data

US 2017/0234757 A1    Aug. 17, 2017

Related U.S. Application Data

(63) Continuation of application No. PCT/CN2014/090083, filed on Oct. 31, 2014.

(51) Int. Cl.
*G01M 3/04* (2006.01)
*B64C 39/02* (2006.01)
(Continued)

(52) U.S. Cl.
CPC ............ *G01M 3/04* (2013.01); *B64C 39/024* (2013.01); *G01M 3/22* (2013.01); *G01N 21/61* (2013.01); *G05D 1/0011* (2013.01); *G05D 1/101* (2013.01); *G08B 7/06* (2013.01); *G08B 13/194* (2013.01); *G08B 17/005* (2013.01); *G08B 21/12* (2013.01); *G08B 25/10* (2013.01); *G08G 5/0069* (2013.01);
(Continued)

(58) Field of Classification Search
None
See application file for complete search history.

(56) References Cited

U.S. PATENT DOCUMENTS 3,662,171 A * 5/1972 Brengman ............ G01M 3/002
                                                    250/337
4,132,943 A * 1/1979 Gournay ................ G01V 9/005
                                                    324/335
(Continued)

FOREIGN PATENT DOCUMENTS

CN        1321846 A      11/2001
CN      102066194 A       5/2011
(Continued)

OTHER PUBLICATIONS

The World Intellectual Property Organization (WIPO) International Search Report for PCT/CN2014/090083 dated Jul. 31, 2015 6 Pages.
(Continued)

*Primary Examiner* — Curtis J King
(74) *Attorney, Agent, or Firm* — Anova Law Group, PLLC

(57) ABSTRACT

A gas leakage treatment method includes detecting a target gas concentration of a target gas in an environment at a corresponding position of a gas delivery pipeline in a process of moving along the gas delivery pipeline. The method further includes, if the target gas concentration is greater than a preset concentration threshold, determining that gas leakage occurs and performing a gas leakage treatment operation.

17 Claims, 9 Drawing Sheets

(51) Int. Cl.
*G01N 21/61* (2006.01)
*G05D 1/00* (2006.01)
*G05D 1/10* (2006.01)
*G08B 7/06* (2006.01)
*G08G 5/00* (2006.01)
*G01M 3/22* (2006.01)
*G08B 13/194* (2006.01)
*G08B 17/00* (2006.01)
*G08B 21/12* (2006.01)
*G08B 25/10* (2006.01)

(52) U.S. Cl.
CPC .... *B64C 2201/12* (2013.01); *B64C 2201/123* (2013.01); *B64C 2201/127* (2013.01); *B64C 2201/141* (2013.01)

(56) References Cited

U.S. PATENT DOCUMENTS

| | | | | |
|---|---|---|---|---|
| 4,853,543 | A * | 8/1989 | Ozdemir | G01N 21/39 250/338.5 |
| 5,045,937 | A * | 9/1991 | Myrick | G01J 5/007 348/144 |
| 5,166,789 | A * | 11/1992 | Myrick | G01V 9/00 348/144 |
| 5,272,646 | A | 12/1993 | Farmer | |
| 5,742,053 | A * | 4/1998 | Rekunyk | G01M 3/38 250/253 |
| 8,358,420 | B1 * | 1/2013 | DeWitt | G01J 3/45 356/450 |
| 2003/0236597 | A1 * | 12/2003 | Andersen | F17D 5/06 701/3 |
| 2004/0189976 | A1 * | 9/2004 | Burns | G01N 1/26 356/28.5 |
| 2004/0232338 | A1 * | 11/2004 | Tolton | G01N 21/3518 250/338.5 |
| 2004/0263852 | A1 * | 12/2004 | Degtiarev | G01M 3/38 356/437 |
| 2005/0024634 | A1 * | 2/2005 | Barker | G01N 21/658 356/301 |
| 2005/0134859 | A1 * | 6/2005 | Kalayeh | G01N 21/31 356/437 |
| 2006/0268947 | A1 * | 11/2006 | Kalayeh | G01N 21/3504 372/20 |
| 2011/0181279 | A1 * | 7/2011 | Srnka | G01N 24/08 324/307 |
| 2013/0289899 | A1 * | 10/2013 | Tolton | G01M 3/00 702/51 |
| 2014/0336928 | A1 * | 11/2014 | Scott | G01N 21/88 701/468 |
| 2015/0210388 | A1 * | 7/2015 | Criado | B64C 39/10 701/3 |
| 2017/0089829 | A1 * | 3/2017 | Bartholomew | G01J 3/0254 |

FOREIGN PATENT DOCUMENTS

| | | |
|---|---|---|
| CN | 102422155 A | 4/2012 |
| CN | 202757738 U | 2/2013 |
| WO | 9641097 A1 | 12/1996 |
| WO | 2005015326 A1 | 2/2005 |

OTHER PUBLICATIONS

Haibin Wu, The Study on Application of UAV in Inspection of Oil and Gas Pipelines, China Petroleum and Chemical Standard and Quality, 2014, Issue 9, Beijing, China.

* cited by examiner

GAS LEAKAGE TREATMENT METHOD AND AERIAL VEHICLE

CROSS-REFERENCE TO RELATED APPLICATION

This is a continuation application of International Application No. PCT/CN2014/090083, filed on Oct. 31, 2014, the entire contents of which are incorporated herein by reference.

TECHNICAL FIELD

The present disclosure generally relates to the technical field of gas leakage detection, and in particular, to gas leakage treatment methods and aerial vehicles.

BACKGROUND

Transportation of gases such as natural gas is generally implemented through a pipeline, and the pipeline used for the transportation needs to have suitable strength and stiffness, so as to ensure that a gas delivery pipeline can withstand external forces, for example, the pipeline needs to withstand the pressure of snow accumulation, soil pressure, even the three produced by earthquake disasters and so on.

In existing technology, gas (such as natural gas) leakage detection of pipelines is basically carried out through manual inspection, which consumes manpower and is not conductive to pipeline gas leakage detection.

SUMMARY OF THE DISCLOSURE

Embodiments of the present disclosure, provide gas leakage treatment methods and aerial vehicles, which can automatically and intelligently complete detection work of whether there is target gas leakage in to gas delivery pipeline.

In one aspect, the embodiments of the present disclosure provide a gas leakage treatment method including detecting a target gas concentration of a target gas in an environment at a corresponding position of a gas delivery pipeline in a process of moving along the gas delivery pipeline. The method further includes, lithe target gas concentration is greater than a preset concentration threshold, determining that gas leakage occurs and performing a gas leakage treatment operation.

In some embodiments, the method further includes, before detecting the target gas concentration, controlling a mobile detection device to move along the gas delivery pipeline. The mobile detection device is configured to detect the target gas concentration in the environment at the corresponding position of the gas delivery pipeline in the process of moving along the gas delivery pipeline.

In some embodiments, the mobile detection device includes an aerial vehicle configured to detect a gas concentration. Controlling the mobile detection device to move along the gas delivery pipeline includes generating flight path information according to acquired installation position trajectory information of the gas delivery pipeline and controlling the aerial vehicle to fly along a path indicated by the flight path information, or shooting an image that includes a visual pattern disposed on the gas delivery pipeline and controlling the aerial vehicle to fly along the gas delivery pipeline according to feature points on the visual pattern in the shot image.

In some embodiments, controlling the mobile detection device to move along the gas delivery pipeline further comprises, in the course of the flight of the aerial vehicle, if calibration information sent by a calibrator disposed on the gas delivery pipeline is received, correct flight data of the aerial vehicle according to the received calibration information. The flight data includes a flight position, or the flight position and a flight attitude.

In some embodiments, the mobile detection device is coupled with an air chamber exposed to the air. Detecting the target gas concentration includes controlling the mobile detection device to be in a stationary state at the corresponding position, starting timing when the detection device enters the stationary state, and, when a timing duration reaches a preset duration threshold, performing a gas analysis operation on gas in the air chamber to determine the target gas concentration in the air chamber.

In some embodiments, the target gas includes natural gas, and the gas analysis operation includes a non-dispersive infrared gas analysis operation.

In some embodiments, performing the gas leakage treatment operation includes sending an alarm indication signal or sending an indication signal that carries a position coordinate.

In some embodiments, detecting the target gas concentration includes, in the process of moving along the gas delivery pipeline, detecting the target gas concentration in the environment at the corresponding position of the gas delivery pipeline according to a preset detection interval. The preset detection interval includes a detection time interval or a moving distance interval. In some embodiments, detecting the target gas concentration includes, in the process of moving along the gas delivery pipeline, detecting whether a position indicated by a preset position coordinate is reached and, if the position indicated by the preset position coordinate is reached, detecting the target gas concentration in the environment of the gas delivery pipeline at the position.

In some embodiments, detecting the target gas concentration includes, in the process of moving along the gas delivery pipeline, judging whether detection trigger information is acquired and, if the detection trigger information is acquired, detecting the target gas concentration of the environment of the gas delivery pipeline at a current position.

In some embodiments, judging whether the detection trigger information is acquired includes, in the process of moving along the gas delivery pipeline, collecting a visual image in real time and, if the collected visual image includes a pattern used for indicating performing target gas concentration detection, determining that the detection trigger information is acquired. In some embodiments, judging whether the detection trigger information is acquired includes, in the process of moving along the gas delivery pipeline, if a wireless signal used fur indicating performing the target gas concentration detection is received, determining that the detection trigger information is acquired.

In some embodiments, the method further comprising, before detecting the target gas concentration, detecting whether an ambient temperature is lower than a preset temperature threshold and, if the ambient temperature is lower than the preset threshold, performing a temperature compensation operation.

In another aspect, the embodiments of the present disclosure further provide an aerial vehicle including a power assembly, a flight controller configured to control a power output of the power assembly to make the aerial vehicle move along a gas delivery pipeline, and a gas detection device configured to detect a target gas concentration of a target gas in an environment at a corresponding position of the gas delivery pipeline in a process of moving along the gas delivery pipeline. If the target gas concentration is greater than a preset concentration threshold, the gas detection device determines that gas leakage occurs and performs a gas leakage treatment operation.

In some embodiments, the flight controller is further configured to control the power output of the power assembly according to installation position trajectory information of the gas delivery pipeline. In some embodiments, the aerial vehicle further includes an image collection device configured to collect an image of a visual pattern preset on the gas delivery pipeline, and the flight controller is further configured to control the aerial vehicle to fly along the gas delivery pipeline according to feature points on the visual pattern in the image obtained by the image collection device.

In some embodiments, the aerial vehicle further includes a communication device configured to receive an external signal. The flight controller is further configured to, in the course of the flight of the aerial vehicle, if the communication device receives calibration information sent by a calibrator disposed on the gas delivery pipeline, control the power output of the power assembly according to the received calibration information, to correct flight data of the aerial vehicle. The flight data includes a flight position, or the flight position and a flight attitude.

In some embodiments, the gas detection device is further configured to, in the process of moving along the gas delivery pipeline, detect the target gas concentration in the environment at the corresponding position of the gas delivery pipeline according to, a preset detection interval. The preset detection interval includes a detection time interval or a moving distance interval. In some embodiments, the gas detection device is further configured to, in the process of moving along the gas delivery pipeline, detect whether a position indicated by a preset position coordinate is reached and, if the position indicated by the preset position coordinate is reached, detect the target gas concentration in the environment of the gas delivery pipeline at the position.

In some embodiments, the gas detection device is further configured to, in the process of moving along the gas delivery pipeline, judge whether detection trigger information is acquired and, if the detection trigger information is acquired, detect the target gas concentration of the environment of the gas delivery pipeline at a current position.

In some embodiments, the gas detection device is further configured to, in the process of moving along the gas delivery pipeline, collect a visual image in real time and, if the collected visual image includes a pattern used for indicating performing target gas concentration detection, determine that the detection trigger information is acquired. In some embodiments, the gas detection device is further configured to, in the process of moving along the gas delivery pipeline, if a wireless signal used for indicating performing target gas concentration detection is received, determine that the detection trigger information is acquired.

In some embodiments, the aerial vehicle further includes an air chamber coupled to the gas detection device. The air chamber is exposed to the air. The gas detection device is further configured to control the mobile detection device to be in a stationary state at the corresponding position, start timing when the detection device enters the stationary state, and, when a timing duration reaches a preset duration threshold, perform a gas analysis operation on gas in the air chamber, to determine the target gas concentration in the air chamber.

In some embodiments, the gas detection device is further configured to, if the target gas concentration is greater than the preset concentration threshold, determine that gas leakage occurs and send an alarm indication signal. In some embodiments, the gas detection device is further configured to, if the target gas concentration is greater than the preset concentration threshold, determine that gas leakage occurs and send an indication signal that carries a position coordinate.

In some embodiments, the aerial vehicle further includes a temperature compensation device configured to detect whether an ambient temperature is lower than a preset temperature threshold and, if the ambient temperature is lower than the preset temperature threshold, perform a temperature.

According to the embodiments of the present disclosure, it is possible to perform mobile detection of the concentration of target gas in the air, so as to determine whether or not a gas leakage occurs in a gas delivery pipeline, and corresponding operations, such alarm, position notification and even automatic leakage blocking can be automatically completed, which meets users' demand for automatically and intelligently detecting gas leakage and reduces the cost of detecting gas leakage.

DETAILED DESCRIPTION OF THE DISCLOSURE

The technical solutions in the embodiments of the present disclosure will be described in detail below with reference to the accompanying drawings of the present disclosure. Obviously, the described embodiments are merely some of the embodiments of the present disclosure rather than all of the embodiments. All other embodiments obtained by a person of ordinary skill in the art based on the embodiments of the present disclosure without creative efforts shall fall within the protection scope of the present disclosure.

According to the embodiments of the present disclosure, it is possible to, in a process where a mobile detection device moves along a natural gas input pipeline, automatically detect whether or not leakage occurs at a corresponding position of a gas delivery pipeline according to a user demand. The mobile detect on device includes: a UAV (Unmanned Aerial Vehicle), a remote control car, a remote control robot, or the like.

Figure 1:
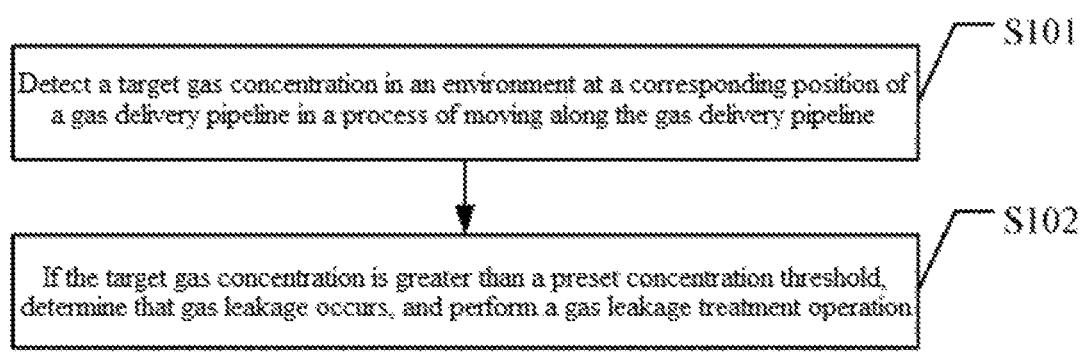
FIG. 1 is a schematic flow chart of one gas leakage treatment method according to an embodiment of the present disclosure.

FIG. 1 is a schematic flow chart of one gas leakage treatment method according to an embodiment of the present disclosure. Referring to FIG. 1, the method according to the embodiments of the present disclosure can be implemented by a processor, and the method according to this embodiment of the present disclosure comprises:

S101: A target gas concentration in an environment at a corresponding position of a gas delivery pipeline is detected in a process of moving along the gas delivery pipeline.

It is feasible to make a mobile detection device such as a UAV to fly along a gas delivery pipeline to be detected through manual remote control or automatic movement. Specifically, during automatic flight, it is feasible to, based on data provided by a distance sensor, an image sensor, a GPS positioning sensor and other devices, control the distance between the UAV and the gas delivery pipeline to be within a certain distance range throughout the process, to achieve that the UAV flies along the gas delivery pipeline.

When it is detected that the UAV flies to certain positions, detection on an environment gas at these positions is triggered, the concentration of target gas therein is determined, and the target gas described in the embodiments of the present disclosure may be natural gas, which, in other embodiments, may also be other gases to be detected.

It can be known according to the existing technology that when a beam of monochromatic light is irradiated on a surface of an absorbing medium, after the light passes through the medium of a certain thickness, as the medium absorbs part of light energy, the intensity of transmitted light will be weakened. Based on this principle, it is feasible to irradiate a gas in a certain space with light rays and then determine the concentration of the corresponding gas based on attenuation of the light intensity. Furthermore, as natural gas has strong absorption characteristics for infrared light of which the wavelength is 3.31 um, it is feasible to determine the concentration of the natural gas contained in a certain space through infrared irradiation, which, for example, may be achieved through a non-dispersive infrared gas analysis operation.

Specifically, it is feasible to dispose, in the UAV, an air chamber having an opening in the bottom, and dispose, on two opposite sides of the air chamber, an infrared light transmitting device and an infrared, light receiving device. When the UAV flies to a certain position of the gas delivery pipeline, after the air chamber has been continuously exposed in the air for a period of time, the infrared light transmitting: device and the infrared light receiving device can be turned on to detect the concentration of the natural gas.

In addition, when the target gas concentration in the air chamber is detected, in order to ensure that the detection is not affected by the temperature, it is feasible to enable a temperature compensation operation to compensate for the temperature in the air chamber, and specifically, it is feasible to increase the temperature in the air chamber in order to perform correct measurement of the target gas concentration.

S102: If the target gas concentration is greater than a preset concentration threshold, it is determined that gas leakage occurs, and a gas leakage treatment operation is performed.

The concentration threshold may be configured according to experience, the concentration threshold may be specifically configured according to a distance from the gas delivery pipeline, and it is feasible to correspondingly configure one concentration threshold, for each distance value. When S102 is performed, before comparison, it is feasible to determine a distance from the mobile detection device to the pipeline through a visual or distance sensor or the like, and then select an appropriate concentration threshold as a reference to determine whether or not leakage occurs at the position of the gas delivery pipeline.

If the result of the detection is that the target gas concentration is greater than the preset concentration threshold, it is determined that gas leakage occurs at the detected position, and gas leakage treatment operations to be performed may include sending an alarm signal, for example, a tight-emitting or sounding alarm, or the like, or sending, to a user equipment (a user computer, a user mobile device or a user-held remote controller) indication information that includes a position coordinate. Further, it is also feasible to complete the gas leakage treatment operation in a manner such as automatically brushing sealant within a larger range.

According to the embodiments of the present disclosure, it is possible to perform mobile detection of the concentration of target gas in the air, so as to determine whether or not a gas leakage event occurs in a gas delivery pipeline, and corresponding operations, such as alarm, position notification and even automatic leakage blocking can be automatically completed, which meets users' demand for automatically and intelligently detecting gas leakage and reduces the cost of detecting gas leakage.

Figure 2:
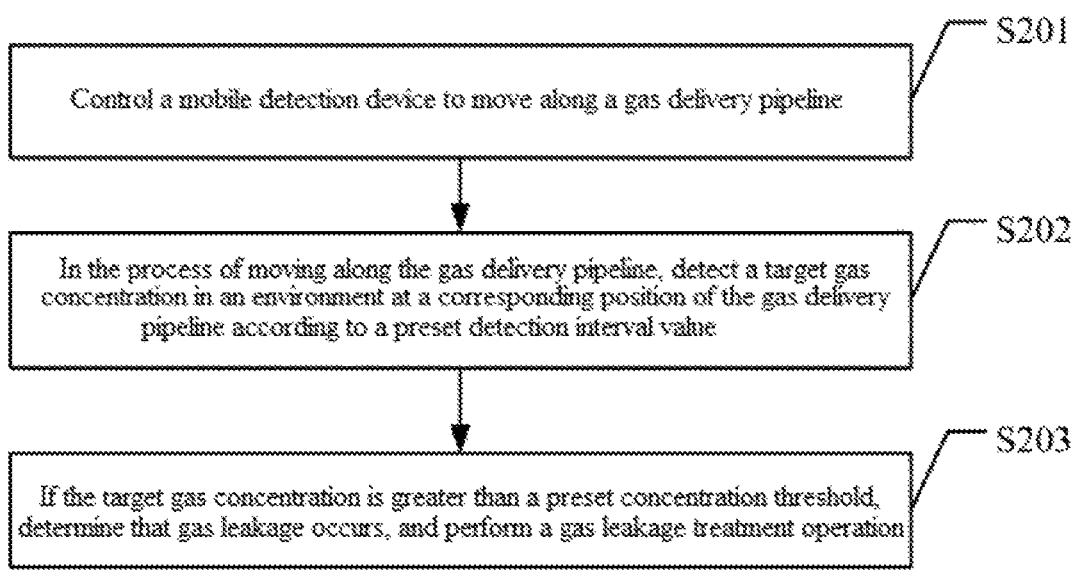
FIG. 2 is a schematic flow chart of another gas leakage treatment method according to another embodiment of the present disclosure.

FIG. 2 is a schematic flow chart of a gas leakage treatment method according to another embodiment of the present disclosure. Referring to FIG. 2, the method according to the embodiments of the present disclosure may be implemented by a processor, the processor may be configured in such as a UAV (Unmanned Aerial Vehicle). Specifically, the method according to this embodiment of the present disclosure comprises:

S201: A mobile detection device is controlled to move along a gas delivery pipeline;

S202: In the process of moving along the gas delivery pipeline, a target gas concentration in an environment at a corresponding position of the gas delivery pipeline is detected according to a preset detection interval value; and the preset detection interval value may include: a detection time interval value or a moving distance interval value.

The time interval may be calculated through a timer, for triggering detection of the target gas concentration. The distance interval may be calculated according to a coordinate output by a built-in GPS module, for example, to obtain a distance interval of flight movement.

The mobile detection device may be provided with an air chamber exposed to the air, after the air chamber is placed in an environment at a corresponding position of the gas delivery pipeline for a period of time, an environment gas may be filled into the air chamber, in order to perform gas leakage detection. Specifically, performance of the target gas concentration detection at S202 may include:

controlling the mobile detection device to be in a stationary state at the corresponding position; and starting timing from when the detection device is put in the stationary state, and when a timing duration reaches a preset duration threshold, performing a gas analysis operation on gas in the air chamber, to determine a target gas concentration in the air chamber.

The purpose of setting the mobile detection device to be in a stationary state is to fully acquire various gases in the environment, in order to detect the target gas concentration more accurately. The gas analysis operation on a gas entering into the air chamber may, based on actual needs, include a non-dispersive infrared gas analysis operation or the like.

Specifically, in the process of detecting the target gas concentration, to overcome influences of the environmental temperature on gas concentration detection, it is feasible to, in the detection process, perform a temperature compensation operation when the environmental temperature is too low.

S203: If the target gas concentration is greater than a preset concentration threshold, it is determined that gas leakage occurs, and a gas leakage treatment operation is performed.

Specifically, S203 may include: if the target gas concentration is greater than the preset concentration threshold, determining that gas leakage occurs, and sending an alarm indication signal; or if the target gas concentration is greater than the preset concentration threshold, determining that gas leakage occurs, and sending an indication signal that carries a position coordinate.

Specifically, when the concentration of the target gas in the air detected is greater than the preset concentration threshold, it is feasible to directly send an alarm to the control users nearby through a sounding or light-emitting alarm device configured in the mobile detection device. Alternatively, an indication signal that carries the GPS coordinate data of the position is sent to a designated user directly through a wireless communication module.

According to the embodiments of the present disclosure, it is feasible to detect whether or not a gas leakage event occurs in a gas delivery pipeline based on a time interval or a distance interval, and corresponding operations, such as alarm, position notification and even automatic leakage blocking can be automatically completed, which meets users' demand for automatically and intelligently detecting gas leakage and reduces the cost of detecting gas leakage.

Figure 3:
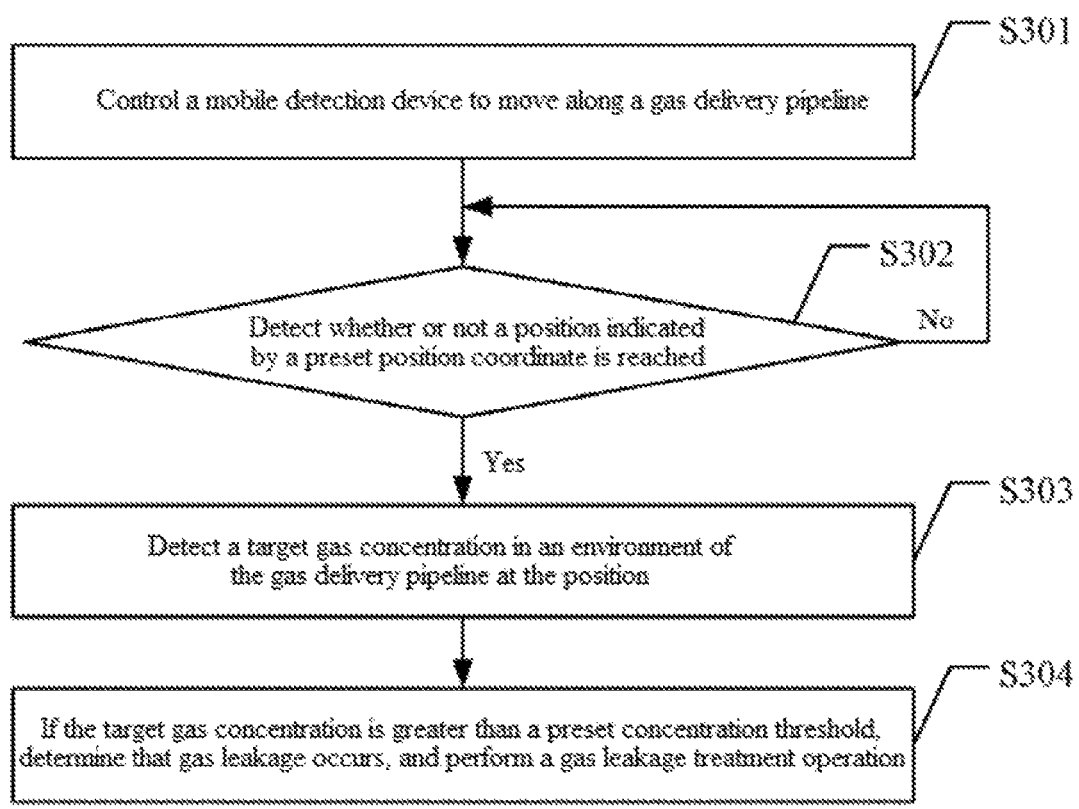
FIG. 3 is a schematic flow chart of a further gas leakage treatment method according to anther embodiment of the present disclosure.

FIG. 3 is a schematic flow chart of another gas leakage treatment method according to another embodiment of the present disclosure. Referring to FIG. 3, the method according to the embodiments of the present disclosure may be implemented by a processor, the processor may be configured in such as a UAV. Specifically, the method according to this embodiment of the present disclosure comprises:

S301: A mobile detection device is controlled to move along a gas delivery pipeline;

S302: In the process of moving along the gas delivery pipeline, whether or not a position indicated by a preset position coordinate is reached is detected;

The preset position coordinate may be configured by a user based on a GPS coordinate. When a GPS coordinate value output by a built-in GPS module in the mobile detection device is close to or reaches the preset position coordinate, detection of a target gas concentration is triggered, the following S303 is performed, and otherwise, a GPS coordinate output by the built-in GPS module and the preset position coordinate are parsed and compared. It should be noted that the preset position coordinate may be a regional position coordinate, that is, a coordinate range, and after a comparison result determines that the mobile detection device enters into the preset region, execution of the following S303 is triggered.

S303: If yes, a target gas concentration in an environment of the gas delivery pipeline at the position is detected.

The mobile detection device is provided with, an air chamber exposed to the air, after the air chamber is present in an environment at a corresponding position of the gas delivery pipeline for a period of time, an environment gas may be filled into the air chamber, in order to perform gas leakage detection. Specifically, when the target gas concentration detection is performed, S303 may include:

controlling the mobile detection device to be in a stationary state at the corresponding position; and starting timing from when the detection device is put in the stationary state, and when a timing duration reaches a preset duration threshold, performing a gas analysis operation on gas in the air chamber, to determine a target gas concentration in the air chamber.

The purpose of making the mobile detection device in a stationary state is to fully acquire various gases in the environment, in order to detect a more accurate target gas concentration. The gas analysis operation on a gas entering into the air chamber may, based on actual needs, include a non-dispersive infrared gas analysis operation or the like.

Specifically, in the process of detecting the target gas concentration, to overcome influences of the environmental temperature on gas concentration detection, it is feasible to, in the detection process, perform a temperature compensation operation when the environmental temperature is too low.

S304 if the target gas concentration is greater than a preset concentration threshold, it is determined that gas leakage occurs, and a gas leakage treatment operation is performed;

Specifically, S304 may include: if the target gas concentration is greater than the preset concentration threshold, determining that gas leakage occurs, and sending an alarm indication signal; or if the target gas concentration is greater than the preset concentration threshold, determining that gas leakage occurs, and sending an indication signal that carries a position coordinate.

It is feasible to directly send an alarm to the control users nearby through a sounding or light-emitting alarm device configured in the mobile detection device. Alternatively, an indication signal that carries GPS coordinate data of the position is sent to a designated user directly through a wireless communication module.

According to the embodiment of the present disclosure, it is feasible to detect whether or not a gas leakage event occurs in a gas delivery pipeline at a position configured by a user, and corresponding operations, such as alarm, position notification and even automatic leakage blocking can be automatically completed, which meets users' demand for automatically and intelligently detecting gas leakage and reduces the cost of detecting gas leakage.

Figure 4:
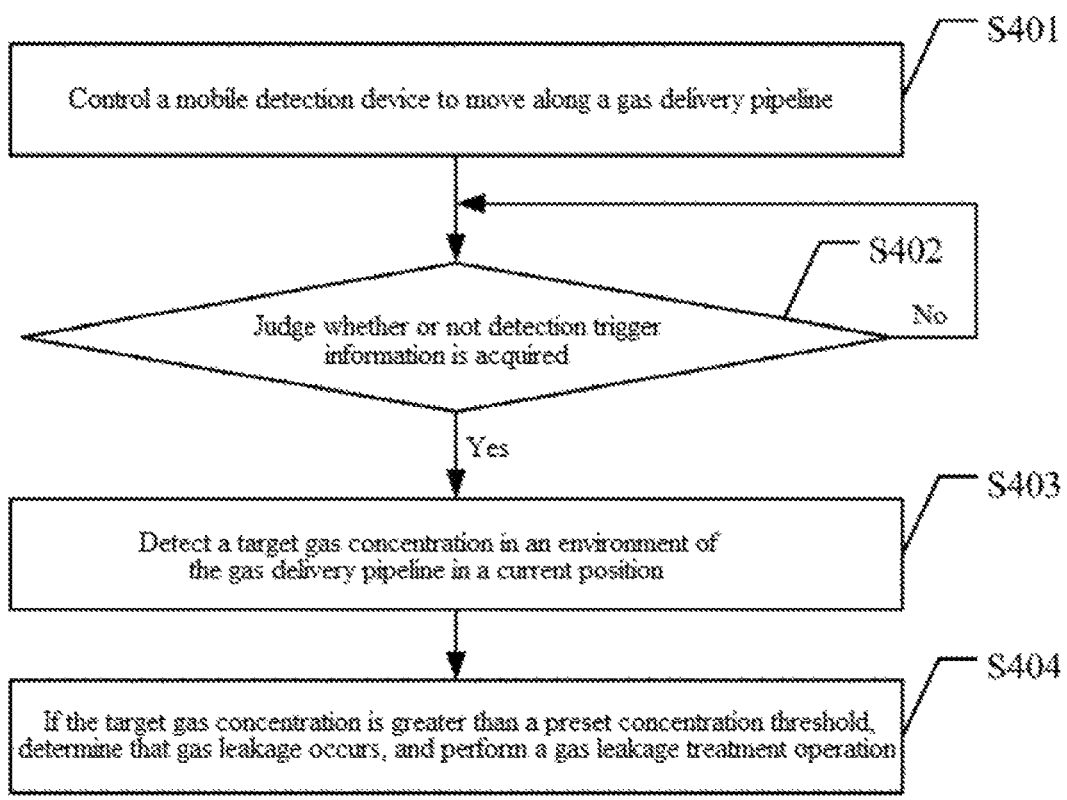
FIG. 4 is a schematic flow chart of a yet another gas leakage treat method according to another embodiment of the present disclosure.

FIG. 4 is a schematic flow chart of another gas leakage treatment method according to another embodiment of the present disclosure. Referring to FIG. 4, the method according to the embodiments of the present disclosure may be implemented by a processor, the processor may be configured in such as a UAV. Specifically, the method according to this embodiment of the present disclosure comprises:

S401: A mobile detection device is controlled to move along a gas delivery pipeline;

S402: In the process of moving along the gas delivery pipeline, whether or not detection trigger information is acquired is judged;

Wherein, in this embodiment of the present disclosure, S402 may include: in the process of moving along the gas delivery pipeline, collecting a visual image in real time, and if the collected visual image comprises a pattern used tier indicating performing target gas concentration detection, determining that the detection trigger information is acquired. It is feasible to use a shooting module such as a video camera disposed in the mobile detection device to collect image information, and a user can set patterns in particular colors and shapes on the pipeline at particular positions of other delivery pipelines through painting or sticking a ribbon in advance, to facilitate visual identification. The patterns in particular colors and shapes can be set very obviously, to make it convenient to perform identification.

Alternatively, S402 may further include: in the process of moving along the gas delivery pipeline, if a wireless signal, used for indicating performing target gas concentration detection is received, determining that the detection trigger information is acquired.

By directly disposing a wireless signal transmitter on the pipeline and transmitting a signal at a particular frequency, a detection device such as an Unmanned Aerial Vehicle may be accurately triggered to detect an environment gas at a position when a wireless trigger signal is received. It may be more accurate to trigger gas concentration detect by a wireless signal.

If a particular visual pattern is detected or a wireless signal at a particular frequency is received, the following S403 is performed, in which a target gas concentration is detected, and otherwise, S402 is continuously performed.

S403: If detection trigger information is acquired, target gas concentration in an environment of the gas delivery pipeline in a current positions detected.

The mobile detection device may be provided with an air chamber exposed to the air, after the air chamber is present in an environment at a corresponding position of the gas delivery pipeline for a period of time, an environment gas may be filled into the air chamber, in order to perform gas leakage detection. Specifically, when detection of the target gas concentration is performed, S403 may include:

controlling the mobile detection device to be in a stationary state at the corresponding position; and starting timing from when the detection device is put in the stationary state, and when a timing duration reaches a preset duration threshold, performing a gas analysis operation on gas in the air chamber, to determine a target gas concentration in the air chamber.

The purpose of making the mobile detection device in a stationary state is to fully acquire various gases in the environment, in order to detect a more accurate target gas concentration. The gas analysis operation on a gas entering into the air chamber may, based on actual needs, include a non-dispersive infrared gas analysis operation or the like.

Specifically, in the process of detecting: the target gas concentration, to overcome influences of the environmental temperature on gas concentration detection, it is feasible to, in the detection process, perform a temperature compensation operation when the environmental temperature is too low.

S404: If the target gas concentration is greater than a preset concentration threshold, it is determined that gas leakage occurs, and a gas leakage treatment operation is performed;

Specifically, S404 may include: if the target gas concentration is greater than the preset concentration threshold, determining that gas leakage occurs, and sending an alarm indication signal; or if the target gas concentration is greater than the preset concentration threshold, determining that gas leakage occurs, and sending an indication signal that carries a position coordinate.

It is feasible to directly send an alarm to control users nearby through a sounding or light-emitting alarm device configured in the mobile detection device. Alternatively, an indication signal that carries GPS coordinate data of the position is sent to a designated user directly through a wireless communication module.

According to the embodiments of the present disclosure, it is feasible to trigger detection of whether or not a gas leakage event occurs in a gas delivery pipeline based on manners such as visual or wireless communication. Corresponding operations, such as alarm, position notification and even automatic leakage blocking can be automatically completed, which meets users' demand for automatically and intelligently detecting gas leakage and reduces the cost of detecting gas leakage.

Figure 5:
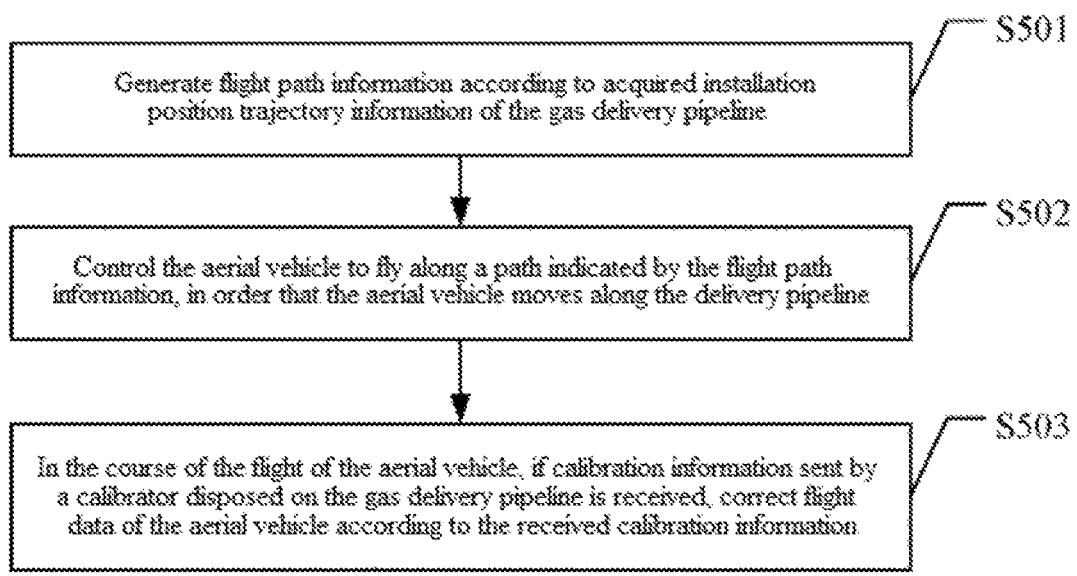
FIG. 5 is a schematic flow chart of one method of controlling a mobile detection device to move along a gas delivery pipeline according to an embodiment of the present disclosure.

FIG. 5 is a schematic flow chart of one method of controlling a mobile detection device to move along a gas delivery pipeline according to an embodiment of the present disclosure. Referring to FIG. 5, this embodiment of the present disclosure corresponds to a mobile control manner of the mobile detection device described in the'above embodiments. Specifically, in this embodiment of the present disclosure the mobile detection device is an aerial vehicle used for detecting a gas concentration and may specifically be a UAV, and the method comprises:

S501: Flight path information is generated according to acquired installation position trajectory information of the gas delivery pipeline;

S502: The aerial vehicle is controlled to fly along a path indicated by the flight path information, in order that the aerial vehicle moves along the delivery pipeline.

Optionally, the control method according to this embodiment of the present disclosure may further include: S503: in the course of the flight of the aerial vehicle, if calibration information sent by a calibrator disposed on the gas delivery pipeline is received, correcting flight data of the aerial vehicle according to the received calibration information; and the flight data may include: flight positions, or flight positions and flight attitudes.

In most cases, a coordinate value of a gas input pipeline is known, and based on the coordinate value, corresponding position parameters and flight altitude parameters are set, to complete configuration of a flight path. The aerial vehicle may use a built-in GPS module and an altitude sensor such as a barometer, to ensure that it flies along the configured flight path. In the course of the flight of the aerial vehicle, it is feasible to adjust the position of the aerial vehicle and flight attitudes such as flight paths, by a calibrator disposed on the gas input pipeline which can send a wireless signal.

According to the embodiments of the present disclosure, it is feasible to configure an automatic flight trajectory of an aerial vehicle based on a trajectory of the pipeline, which meets users' demand for automatically and intelligently detecting gas leakage of a delivery pipeline.

Figure 6:
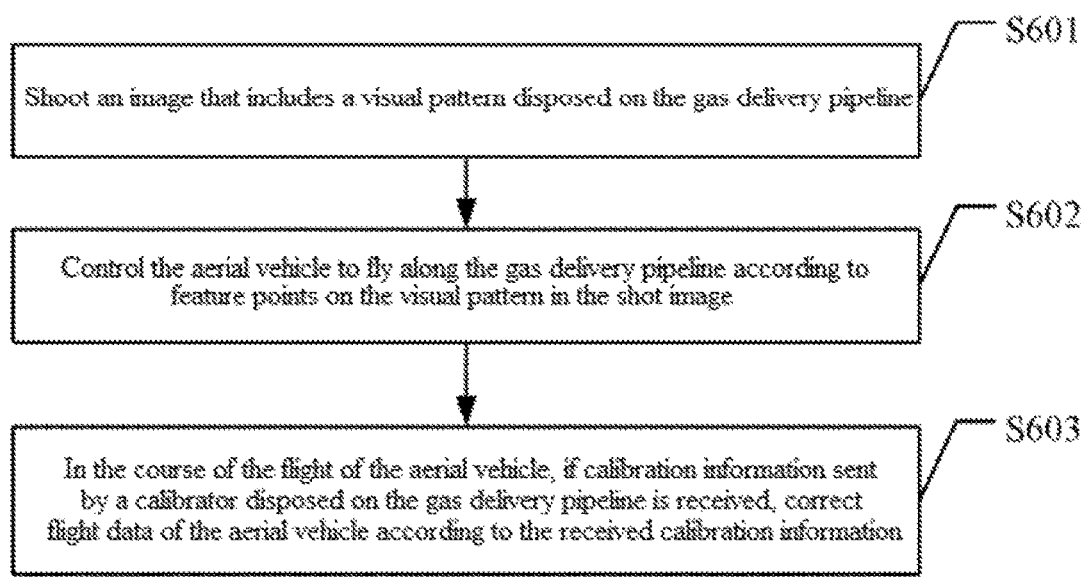
FIG. 6 is a schematic flow chart of another method of controlling a mobile detection deice to move along a gas delivery pipeline according to another embodiment of the present disclosure.

FIG. 6 is a schematic flow chart of another method of controlling a mobile detection device to move along a gas delivery pipeline according to another embodiment of the present disclosure. Referring to FIG. 6, this embodiment of the present disclosure corresponds to a mobile control method of the mobile detection device described in the above embodiments. Specifically, in this embodiment of the present disclosure, the mobile detection device is an aerial vehicle used for detecting a gas concentration and may specifically be a UAV, and the method comprises:

S601: An image that includes a visual pattern disposed on the gas delivery pipeline is shot;

S602: The aerial vehicle is controlled to fly along the gas delivery pipeline according to feature points on the visual pattern in the shot image.

Optionally, the control method according to this embodiment of the present disclosure may further include: S603: in the course of the flight of the aerial vehicle, if calibration information sent by a calibrator disposed on the gas delivery pipeline is received, correcting flight data of the aerial vehicle according to the received calibration information; and the flight data may include: flight positions, or flight positions and flight attitudes.

It is feasible to collect and analyze a particular visual pattern using a high definition camera disposed in the aerial vehicle, to control the aerial vehicle to fly along the gas delivery pipeline. Specifically, it is feasible to, based on a corresponding relationship between the color and the vertex of the visual pattern disposed on the gas delivery pipeline and a preset actual pattern size, obtain a set of three-dimensional coordinate points in a real world coordinate system and two-dimensional image coordinates of corresponding images. It is then possible to use a common PNP (Perspective N Points) algorithm to determine the distance (local coordinates) and the direction of the aerial vehicle, relative to a corner point of the corresponding pattern. Based on the actual GPS coordinates and absolute altitude of the corner point, it is possible to determine and adjust the GPS coordinates and the altitude of the aerial vehicle, According to the embodiments of the present disclosure, it is feasible to control an aerial vehicle to fly based on a visual pattern disposed on a pipeline, which meets users' demand for automatically and intelligently detecting gas leakage of a delivery pipeline.

The gas leakage treatment devices and the aerial vehicles according to the embodiments of the present disclosure are described below in detail.

Figure 7:
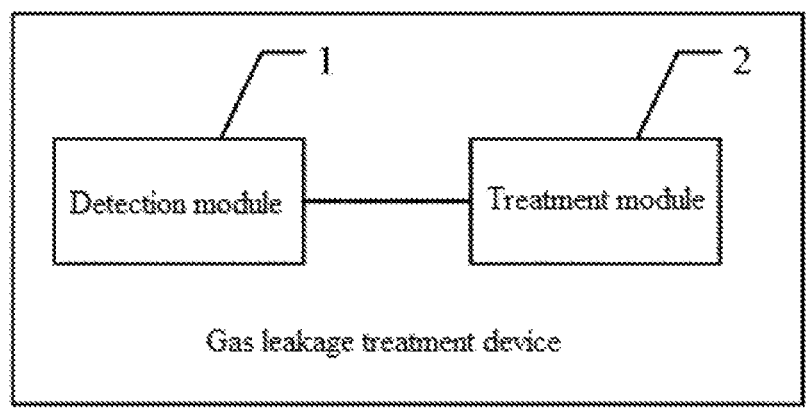
FIG. 7 is a schematic structural diagram of one gas leakage treatment device according to an embodiment of the present disclosure.

Referring to FIG. 7, FIG. 7 is a schematic structural diagram of one gas leakage treatment device according to an embodiment of the present disclosure. The devices according to the embodiments of the present disclosure may be configured in various kinds of movable machines, for example, it may be configured in a UAV. Referring to FIG. 7, the device according to this embodiment comprises:

a detection module 1 used for detecting a target gas concentration in an environment at a corresponding position of a gas delivery pipeline in a process of moving along the gas delivery pipeline; and a treatment module 2 used for, if the target gas concentration is greater than a preset concentration threshold, determining that gas leakage occurs, and performing a gas leakage treatment operation.

It is feasible to make a mobile detection device such as a UAV to fly along a gas delivery pipeline to be detected through manual remote control or automatic movement. Specifically, during automatic flight, it is feasible to, based on data provided by a distance sensor, an image sensor, a GPS positioning sensor and other devices, control the distance between the UAV and the gas delivery pipeline to be within a certain distance range throughout the process, such that the UAV flies along the gas delivery pipeline.

When detecting that the UAV flies to certain positions, the detection module 1 detects an environment gas at these positions, to determine the concentration of a target gas therein. The target gas in the embodiments of the present disclosure may be natural gas, which, in other embodiments, may also be other gases to be detected.

It can be known according to existing technology that, when a beam of monochromatic light is irradiated on a surface of an absorbing medium, after the light passes through the medium of a certain thickness, as the medium absorbs part of light energy, the intensity of transmitted light will be weakened. Based on this principle, the detection module 1 can irradiate a gas in a certain space with light rays and then determine the concentration of the corresponding gas based on attenuation of the light intensity. Furthermore, as natural gas has strong absorption characteristic for infrared light of which the wavelength is 3.31 um, the detection module 1 can determine the concentration of the natural gas contained in a certain space through infrared irradiation, which may be performed through a non-dispersive infrared gas analysis operation.

Specifically, it is feasible to dispose, in the UAV, an air chamber having an opening in the bottom, and dispose, on two opposite sides of the air chamber, an infrared light transmitting device and an infrared light receiving device. When the UAV flies to a certain position of the gas delivery pipeline, after the air chamber has been continuously exposed in the air for a period of time, the infrared light transmitting device and the infrared light receiving device can be turned on to detect the concentration of the natural gas.

If the result of the detection of the detection module 1 is that the target gas concentration is greater than the preset concentration threshold, it is determined that gas leakage occurs at the detected position. The gas leakage treatment operation performed by the treatment module 2 includes sending an alarm signal, for example, a light-emitting or sounding alarm, or the like, or sending to a user equipment (a user computer, a user mobile device or a user-held remote controller) indication information that includes a position coordinate. Further, the detection module 1 may also complete the gas leakage treatment operation in a manner such as automatically brushing sealant within a larger range.

According to the embodiments of the present disclosure, it is possible to perform mobile detection of the concentration of target gas in the air, so as to determine whether or not a gas leakage event occurs in a gas delivery pipeline. Corresponding operations, such as alarm, position notification and even automatic leakage blocking can be automatically completed, which meets users' demand for automatically and intelligently detecting gas leakage and reduces the cost of detecting gas leakage.

Figure 8:
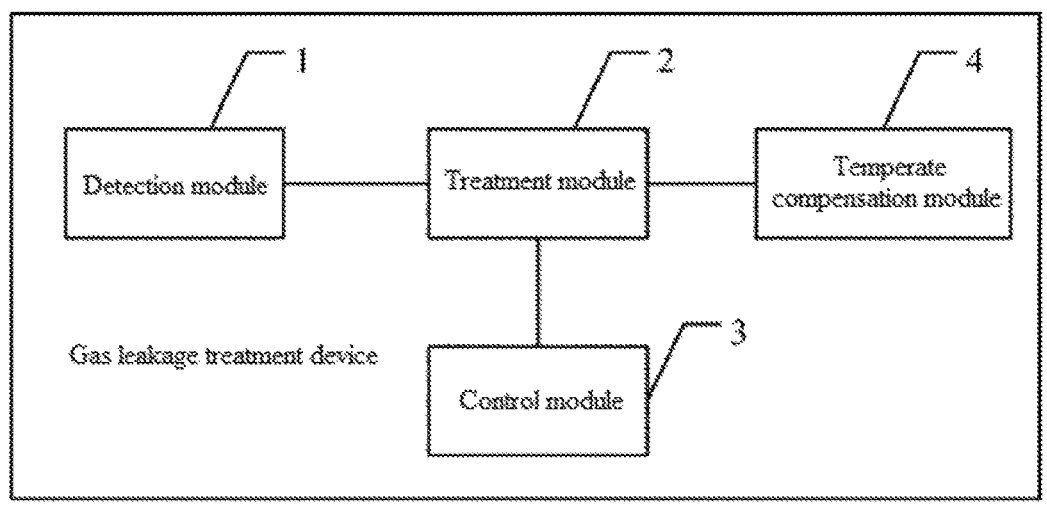
FIG. 8 is a schematic structural diagram of another gas leakage treatment device according to another embodiment of the present disclosure.

FIG. 8 is a schematic structural diagram of another gas leakage treatment device according to another embodiment of the present disclosure. The devices according to the embodiments of the present disclosure may be configured in various kinds of movable machines, for example, it may be configured in a UAV. Referring to FIG. 8, the device in this embodiment comprises the detection module 1 and the treatment module 2 described in the above device embodiment, and further comprises;

a control module 3 used for controlling a mobile detection device to move along the gas delivery pipeline. The control module 3 may serve as a mobile controller of the mobile detection device, for example, a flight controller of a UAV.

Specifically and optionally, the mobile detection device is an aerial vehicle; and the control module 3 is used for generating flight path information according to acquired installation position trajectory information of the gas delivery pipeline; and controlling the aerial vehicle to fly along a path indicated by the flight path information, in order that the aerial vehicle moves along the delivery pipeline. A user can configure coordinate and altitude parameters of the aerial vehicle according to the installation positions and routes of a gas input pipeline, and configure corresponding flight path information in the control module 3, in order that the aerial vehicle can move along the gas delivery pipeline.

Specifically and optionally, the mobile detection device is an aerial vehicle; and the control module 3 is used for shooting an image that includes a visual pattern disposed on the gas delivery pipeline; and controlling the aerial vehicle to fly along the gas delivery pipeline according to feature points on the visual pattern in the shot image. It is feasible to determine the position and the flight attitude of the aerial vehicle relative to the visual pattern based on a PNP algorithm, in order to further control movement of the aerial vehicle.

Specifically and optionally, the control module 3 is further used for, in the course of the flight of the aerial vehicle, if calibration information sent by a calibrator disposed on the gas delivery pipeline is received, correcting flight data of the aerial vehicle according to the received calibration information; and the flight data includes: flight positions, or flight positions and flight attitudes. The calibrators disposed at some special positions on the gas delivery pipeline can send signals at a particular frequency and/or carrying related information (for example, position and attitude information), such that the mobile detection device such as an aerial vehicle can accurately and timely correct the position, the attitude, or the like.

The manner in which the detection module 1 is triggered to detect the target gas concentration includes: it is feasible to trigger the detection of the target gas concentration in the air based on one of a preset time interval, a displacement interval, reaching a designated position, an acquired trigger signal or a trigger image, or a combination thereof.

Specifically and optionally, the detection module 1 may be used for, in the process of moving along the gas delivery pipeline, detecting a target gas concentration in an environment at a corresponding position of the gas delivery pipeline according to a preset detection interval value; and the preset detection interval value may include: a detection time interval value or a moving distance interval value.

The detection module 1 may be used for, in the process of moving along the gas delivery pipeline, detecting whether or not a position indicated by a preset position coordinate is reached; and if yes, detecting a target gas concentration in an environment of the gas delivery pipeline at the position.

The detection module 1 may be used for, in the process of moving along the gas delivery pipeline, judging whether or not detection trigger information is acquired; and if the detection trigger information is acquired, detecting a target gas concentration of an environment of the gas delivery pipeline in a current position.

The detection module 1 may be used for, in the process of moving along the gas delivery pipeline, collecting a visual image in real time, and if the collected visual image comprises a pattern used for indicating performing target gas concentration detection, determining that the detection trigger information is acquired.

The detection module 1 may be specifically used for, in the process of moving along the gas delivery pipeline, if a wireless signal used for indicating performing target gas concentration detection is received, determining that the detection trigger information is acquired.

Specifically and optionally, the detection module 1, when detecting the gas concentration in the air, is used for controlling the mobile detection device to be in a stationary state at the corresponding position; and starting timing from when the detection device is put in the stationary state, and when a timing duration reaches a preset duration threshold, performing a gas analysis operation on gas in the air chamber, to determine a target gas concentration in the air chamber. The detection module 1 may be used for conducting a non-dispersive infrared gas analysis operation that performs concentration detection for natural gas in the air chamber.

Further optionally, the treatment module 2 may be used for, if the target gas concentration is greater than the preset concentration threshold, determining that gas leakage occurs, and sending an alarm indication signal; or if the target gas concentration is greater than the preset concentration threshold, determining that gas leakage occurs, and sending an indication signal that carries a position coordinate.

Further optionally, the device according to some embodiments of the present disclosure may further include:

a temperature compensation module 4 used for detecting whether or not an ambient temperature is lower than a preset temperature threshold, and if yes, performing a temperature compensation operation.

It should be noted that reference can be made to the description of corresponding steps in the embodiments of FIG. 1 to FIG. 6 for the specific implementation of the modules in the devices according to the embodiments of the present disclosure.

According to the embodiments of the present disclosure, it is possible to perform mobile detection of the concentration of target gas in the air, so as to determine whether or not a gas leakage event occurs in a gas delivery pipeline. Corresponding operations, such as alarm, position notification and even automatic leakage blocking can be automatically completed, which meets users' demand for automatically and intelligently detecting gas leakage and reduces the cost of detecting gas leakage.

Figure 9:
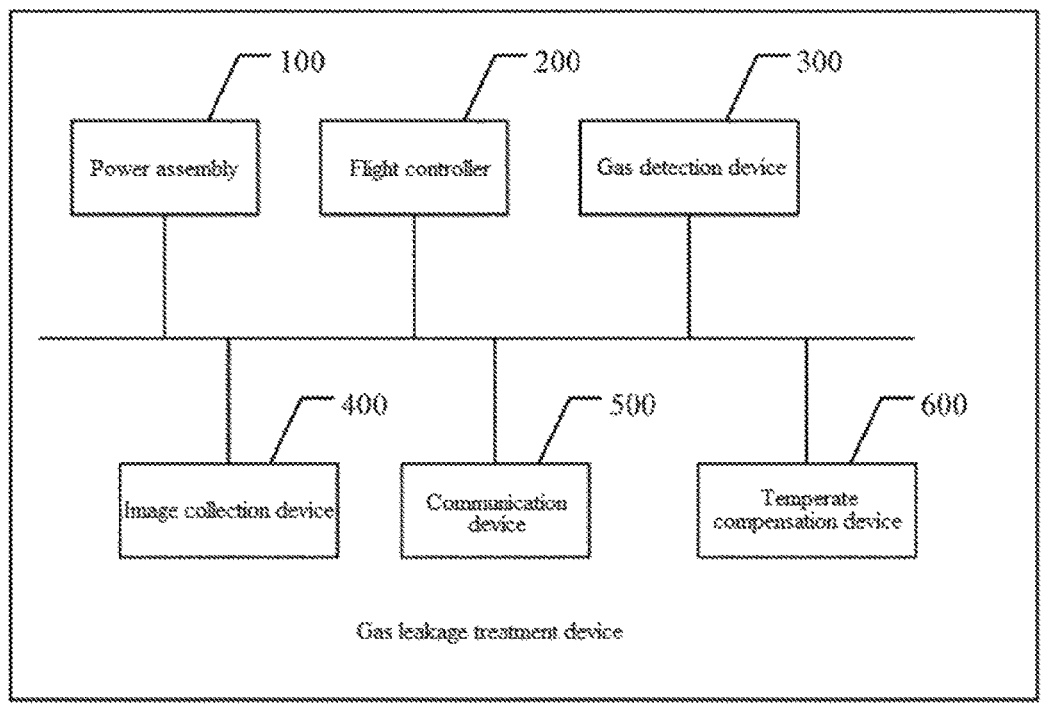
FIG. 9 is a schematic structural diagram of an aerial vehicle according to a embodiment of the present disclosure.

Referring to FIG. 9, FIG. 9 is a schematic structural diagram of an aerial vehicle according to an embodiment of the present disclosure; the aerial vehicle according to this embodiment of the present disclosure includes components such as a propeller and an inertial sensor, as in existing technology. In this embodiment of the present disclosure, the aerial vehicle further includes: a power assembly 100, a flight controller 200 and a gas detection device 100. The gas detection device 300 can execute related programs to perform corresponding functions, wherein:

the flight controller 200 is used for controlling the power output of the power assembly 100, to make the aerial vehicle, move along a gas delivery pipeline; and the gas detection device 300 is used for detecting a target gas concentration in an environment at a corresponding position of a gas delivery pipeline in a process of moving along the gas delivery pipeline; and if the target gas concentration is greater than a preset concentration threshold, determining that gas leakage occurs, and performing a gas leakage treatment operation.

Optionally, the flight controller 200 is used for controlling the power output of the power assembly 100 according to installation position trajectory information of the gas delivery pipeline, in order that the aerial vehicle moves along the delivery pipeline.

Further optionally, the aerial vehicle according to this embodiment of the present disclosure may further include:

an image collection device 400;

the flight controller 200 being used for controlling the aerial vehicle to fly along the gas delivery pipeline according to feature points on the visual pattern in the image obtained by the image collection device.

Further optionally, the aerial vehicle according to this embodiment of the present disclosure further may include: a communication device 500;

the communication device 500 being used for receiving an external signal; and the flight controller 200 being used for, in the course of the flight of the aerial vehicle, if the communication device 500 receives calibration information sent by a calibrator disposed on the gas delivery controlling the power output of the power assembly 100 according to the received calibration information to correct flight data f the aerial vehicle, the flight data including: flight positions, or flight positions and flight attitudes.

Further optionally, the gas detection device 300 of the aerial vehicle according to this embodiment of the present disclosure may be used for, in the process of moving along the gas delivery pipeline, detecting a target gas concentration in an environment at a corresponding position of the gas delivery pipeline according to a present detection interval value. The preset detection interval value may include: a detection time interval value or a moving distance interval value.

Further optionally, the gas detection device 300 of the aerial vehicle according to this embodiment of the present disclosure may be used for, in the process of moving along the gas delivery pipeline, detecting whether or not a position indicated by a preset position coordinate is reached; and if yes, detecting a target gas concentration in an environment of the gas delivery pipeline at the position.

Further optionally, the gas detection device 300 of the aerial vehicle according to this embodiment of the present disclosure may be used for, in the process of moving along the gas delivery pipeline, judging whether or not detection trigger information is acquired; and if the detection trigger information is acquired, detecting a target gas concentration of an environment of the gas delivery pipeline in a current position.

Further optionally, the gas detection device 300 of the aerial vehicle according to this embodiment of the present disclosure may be used for, in the process of moving along the gas delivery pipeline, collecting a visual image in real time, and if the collected visual image comprises a pattern used for indicating performing target gas concentration detection, determining that the detection trigger information is acquired.

Further optionally, the gas detection device 300 of the aerial vehicle according to this embodiment of the present disclosure may be used for, in the process of moving along the gas delivery pipeline, in the process of moving along the gas delivery pipeline, if a wireless signal used for indicating performing target gas concentration detection is received, determining that the detection trigger information is acquired.

Further optionally, the gas detection device 300 of the aerial vehicle according to this embodiment of the present disclosure may be provided with an air chamber exposed to the air, and the gas detection device 300 may be used for controlling the mobile detection device to be in a stationary state at the corresponding position; and starting timing from when the detection device is put in the stationary state, and when a timing duration readies a preset duration threshold, performing a gas analysis operation on gas in the air chamber, to determine a target gas concentration in the air chamber.

Further optionally, the gas detection device 300 of the aerial vehicle according to this embodiment of the present disclosure may be used for, if the target gas concentration is greater than the preset concentration threshold, determining that gas leakage occurs, and sending an alarm indication signal; or if the target gas concentration is greater than the preset concentration threshold, determining that gas leakage occurs, and sending an indication signal that carries a position coordinate.

Further optionally, the aerial vehicle according to this embodiment of the present disclosure may further include: a temperature compensation device 600 used for detecting whether or not an ambient temperature is lower than a preset temperature threshold, and if yes, performing a temperature compensation operation.

It should be noted that reference can be made to the description of the corresponding steps or modules in the corresponding embodiments of FIG. 1 to FIG. 8 for the specific implementation of the devices and parts of the aerial vehicle according to this embodiment of the present disclosure.

According to the embodiments of the present disclosure, it is possible to perform mobile detection of the concentration of target gas in the air, so as to determine whether or not a gas leakage event occurs in a gas delivery pipeline. Corresponding operations, such as alarm, position notification and even automatic leakage blocking can be automatically completed, which meets users' demand for automatically and intelligently detecting gas leakage and reduces the cost of detecting gas leakage.

In the above embodiments provided in the present disclosure, it should be understood that the related devices and methods disclosed may be implemented in other manners. For example, the device embodiments described above are merely explanatory, for example, the division of the modules or units is merely a division based on the logical and divisions in other manners may exist in actual implementation. For example, a plurality of units or assemblies may be combined or integrated to another system, or some features may be omitted or not performed. In addition, the mutual coupling or direct coupling or communication connections displayed or discussed may be implemented by using some interfaces, and the indirect coupling or communication connection between the devices or units may be electrical, mechanical or in another form.

The units described as separate components may be or may not be physically separate, and components presented as units may be or may not be physical units. They may be located in one position, or may be distributed on a plurality of network tints. Some or all of the units may be selected according to actual needs to achieve the objective of the solutions of the embodiments.

In addition, functional units in the embodiments of the present disclosure may be integrated into one processing unit, or each of the units may exist alone physically, or two or more units may be integrated into one unit. The aforementioned integrated units may be implemented in a form of hardware, or may be implemented in a form of a software functional unit.

When the integrated units are implemented in the form of a software functional unit and sold or used as an independent product, the integrated unit may be stored in a computer-readable storage medium. Based on such an understanding, the essence of the technical solutions of the present disclosure, or the part that makes contributions to the prior art, or all or a part of the technical solutions may be implemented in a form of a software product. The computer software product may be stored in a storage medium, and may include several instructions used for causing a computer processor to perform all or a part of the steps of the methods described in the embodiments of the present disclosure. The foregoing storage medium may include: any medium that can store a program code, such as a USB flash drive, a removable hard disk, a Read-Only Memory (ROM), a Random Access Memory (RAM), a magnetic disk, or an optical disc.

The above descriptions are merely exemplary, embodiments of the present disclosure, and are not intended to limit the scope of the present disclosure. Any equivalent structure or equivalent flow transformation made by using contents of the specification and the drawings of the present disclosure, or directly or indirectly applied to other related technical fields, should be likewise included in the scope of the present disclosure.

What is claimed is:

1. A gas leakage treatment method, comprising:
   controlling a mobile detection device to move along a gas delivery pipeline, the mobile detection device being coupled with an air chamber exposed to the air and configured to hold gas;
   detecting, using the mobile detection device, a target gas concentration of a target gas in an environment at a corresponding position of the gas delivery pipeline in a process of moving along the gas delivery pipeline, wherein detecting the target gas concentration comprises:
     controlling the mobile detection device to be in a stationary state at the corresponding position;
     starting timing when the detection device enters the stationary state;
     performing, when a timing duration reaches a preset duration threshold, a gas analysis operation on the gas held in the air chamber to determine the target gas concentration in the air chamber; and
   if the target gas concentration is greater than a preset concentration threshold, determining that gas leakage occurs and performing a gas leakage treatment operation.

2. The method of claim 1, wherein:
   the mobile detection device comprises an aerial vehicle, and
   controlling the mobile detection device to move along the gas delivery pipeline comprises:
     generating flight path information according to acquired installation position trajectory information of the gas delivery pipeline, and controlling the aerial vehicle to fly along a path indicated by the flight path information; or
     shooting an image that includes a visual pattern disposed on the gas delivery pipeline, and controlling the aerial vehicle to fly along the gas delivery pipeline according to feature points on the visual pattern in the shot image.

3. The method of claim 2, wherein controlling the mobile detection device to move along the gas delivery pipeline further comprises:
   in the course of the flight of the aerial vehicle, if calibration information sent by a calibrator disposed on the gas delivery pipeline is received, correcting flight data of the aerial vehicle according to the received calibration information,
   wherein the flight data includes a flight position, or the flight position and a flight attitude.

4. The method of claim 1, wherein the target gas comprises natural gas, and the gas analysis operation comprises a non-dispersive infrared gas analysis operation.

5. The method of claim 1, wherein performing the gas leakage treatment operation comprises:
   sending an alarm indication signal; or
   sending an indication signal that carries a position coordinate.

6. The method of claim 1, wherein detecting the target gas concentration comprises:
   in the process of moving along the gas delivery pipeline, detecting the target gas concentration in the environment at the corresponding position of the gas delivery pipeline according to a preset detection interval, the preset detection interval including a detection time interval or a moving distance interval; or
   in the process of moving along the gas delivery pipeline, detecting whether a position indicated by a preset position coordinate is reached, and, if the position indicated by the preset position coordinate is reached, detecting the target gas concentration in the environment of the gas delivery pipeline at the position.

7. The method of claim 1, wherein detecting the target gas concentration comprises:
   in the process of moving along the gas delivery pipeline, judging whether detection trigger information is acquired; and
   if the detection trigger information is acquired, detecting the target gas concentration of the environment of the gas delivery pipeline at a current position.

8. The method of claim 7, wherein judging whether the detection trigger information is acquired comprises:
   in the process of moving along the gas delivery pipeline, collecting a visual image in real time, and if the collected visual image comprises a pattern used for indicating performing target gas concentration detection, determining that the detection trigger information is acquired; or
   in the process of moving along the gas delivery pipeline, if a wireless signal used for indicating performing the target gas concentration detection is received, determining that the detection trigger information is acquired.

9. The method of claim 1, further comprising, before detecting the target gas concentration:
   detecting whether an ambient temperature is lower than a preset temperature threshold and, if the ambient temperature is lower than the preset threshold, performing a temperature compensation operation.

10. An aerial vehicle, comprising:
    a power assembly;
    a flight controller configured to control a power output of the power assembly to make the aerial vehicle move along a gas delivery pipeline;
    a gas detection device; and
    an air chamber coupled to the gas detection device, the air chamber being exposed to the air and configured to hold gas;
    wherein the gas detection device is configured to:
      detect a target gas concentration of a target gas in an environment at a corresponding position of the gas delivery pipeline in a process of moving along the gas delivery pipeline by:
        controlling the aerial vehicle to be in a stationary state at the corresponding position, starting timing when the aerial vehicle enters the stationary state, and performing, when a timing duration reaches a preset duration threshold, a gas analysis operation on the gas held in the air chamber to determine the target gas concentration in the air chamber, and if the target gas concentration is greater than a preset concentration threshold, determine that gas leakage occurs and perform a gas leakage treatment operation.

11. The aerial vehicle of claim 10, wherein, the flight controller is further configured to control the power output of the power assembly according to installation position trajectory information of the gas delivery pipeline, or the aerial vehicle further comprises an image collection device configured to collect an image of a visual pattern preset on the gas delivery pipeline, and the flight controller is further configured to control the aerial vehicle to fly along the gas delivery pipeline according to feature points on the visual pattern in the image obtained by the image collection device.

12. The aerial vehicle of claim 11, further comprising:

a communication device configured to receive an external signal, wherein the flight controller is further configured to, in the course of the flight of the aerial vehicle, if the communication device receives calibration information sent by a calibrator disposed on the gas delivery pipeline, control the power output of the power assembly according to the received calibration information, to correct flight data of the aerial vehicle, the flight data including a flight position, or the flight position and a flight attitude.

13. The aerial vehicle of claim 10, wherein:

the gas detection device is further configured to, in the process of moving along the gas delivery pipeline, detect the target gas concentration in the environment at the corresponding position of the gas delivery pipeline according to a preset detection interval, the preset detection interval comprising a detection time interval or a moving distance interval; or the gas detection device is further configured to, in the process of moving along the gas delivery pipeline, detect whether a position indicated by a preset position coordinate is reached and, if the position indicated by the preset position coordinate is reached, detect the target gas concentration in the environment of the gas delivery pipeline at the position.

14. The aerial vehicle of claim 10, wherein, the gas detection device is further configured to, in the process of moving along the gas delivery pipeline, judge whether detection trigger information is acquired and, if the detection trigger information is acquired, detect the target gas concentration of the environment of the gas delivery pipeline at a current position.

15. The aerial vehicle of claim 14, wherein, the gas detection device is further configured to, in the process of moving along the gas delivery pipeline, collect a visual image in real time and, if the collected visual image comprises a pattern used for indicating performing target gas concentration detection, determine that the detection trigger information is acquired, or the gas detection device is further configured to, in the process of moving along the gas delivery pipeline, if a wireless signal used for indicating performing target gas concentration detection is received, determine that the detection trigger information is acquired.

16. The aerial vehicle of claim 10, wherein, the gas detection device is further configured to, if the target gas concentration is greater than the preset concentration threshold, determine that gas leakage occurs and send an alarm indication signal, or, if the target gas concentration is greater than the preset concentration threshold, determine that gas leakage occurs and send an indication signal that carries a position coordinate.

17. The aerial vehicle of claim 10, further comprising:

a temperature compensation device configured to detect whether an ambient temperature is lower than a preset temperature threshold and, if the ambient temperature is lower than the preset temperature threshold, perform a temperature compensation operation.

* * * * *